United States Patent [19]

Descotes et al.

[11] Patent Number: 5,344,974
[45] Date of Patent: Sep. 6, 1994

[54] PROCESS FOR THE PREPARATION OF N-ACYL DERIVATIVES OF 5-AMINOLEVULINIC ACID, AS WELL AS THE HYDROCHLORIDE OF THE FREE ACID

[75] Inventors: Gerand Descotes, Lyon; Louis Cottier, Caluire; Laurent Eymard, Malissard, all of France; Knut M. Rapp, Offstein, Fed. Rep. of Germany

[73] Assignee: Sudzucker Aktiengesellschaft Mannheim/Ochensfurt, Mannheim, Fed. Rep. of Germany

[21] Appl. No.: 111,067

[22] Filed: Aug. 24, 1993

[30] Foreign Application Priority Data

Aug. 24, 1992 [DE] Fed. Rep. of Germany ....... 4228084

[51] Int. Cl.$^5$ ........................................... C07C 229/00
[52] U.S. Cl. ................................. 562/567; 204/157.62; 204/157.69; 549/487; 549/496; 562/450
[58] Field of Search ................ 562/567, 450; 549/487, 549/496; 204/157.62, 157.69

[56] References Cited

U.S. PATENT DOCUMENTS

| | | | |
|---|---|---|---|
| 3,846,490 | 11/1974 | Aronova | 562/567 |
| 4,325,877 | 4/1982 | Metcalf | 562/567 |
| 5,095,114 | 3/1992 | Radunz | 562/567 |
| 5,284,973 | 2/1994 | Ebata | 562/567 |

Primary Examiner—Michael L. Shippen
Attorney, Agent, or Firm—Adduci, Mastriani, Schaumberg & Schill

[57] ABSTRACT

The invention relates to a process for the preparation of N-acyl derivatives of 5-aminolevulinic acid of general formula $R-CO-NH-CH_2-CO-CH_2-CH_2-COOH$, in which R stands for methyl, ethyl, propyl, isopropyl, butyl, phenyl, benzyl, furyl or furfuryl, as well as the hydrochloride of the free acid by acid hydrolysis, characterized in that the 5-hydroxymethyl furfural is condensed with a nitrile in acid solution and the N-acyl-aminomethyl furfural compound obtained is converted by photooxidation into a N-acyl-5-aminomethyl-5-hydroxydihydro-2,5-furan-2-one and the latter is reduced with zinc in acetic acid under ultrasonic treatment to N-acyl-5-aminolevulinic acid and by acid hydrolysis the 5-aminolevulinic hydrochloride is obtained.

11 Claims, No Drawings

PROCESS FOR THE PREPARATION OF N-ACYL DERIVATIVES OF 5-AMINOLEVULINIC ACID, AS WELL AS THE HYDROCHLORIDE OF THE FREE ACID

The invention relates to a process for the preparation of N-acyl derivatives of 5-aminolevulinic acid, as well as the hydrochloride of the free, i.e. unsubstituted acid by acid hydrolysis.

δ-aminolevulinic acid or 5-aminolevulinic acid, respectively 5-amino-4-oxopentanoic acid (ALA) is a precursor of vitamin $B_{12}$, heme and chlorophyll and is on the one hand suitable for the biosynthesis of vitamin $B_{12}$ and on the other, also with its derivatives, is of interest as a photodynamic herbicide.

Processes for the preparation of ALA as hydrochloride starting from tetrahydrofurfuryl amine or furfural have been described by H. Kawakami et al in Agric. Biol. Chem., 1991, 56, pp 1687/8 and K. Suzuki et al in JA-03072450-A 2. However, the yields in these multistage processes are relatively low.

The preparation of ALA as hydrochloride by acid hydrolysis of other heterocycles such as piperidine-2,5-dione has been described by C. Herdeis et al in Arch. Pharm., 1984, 317, pp 304–306. Through the hydrolysis of oxazolinone ALA is obtained according to W. Shen et al in Youji Huaxue, 1987, pp 278–280 or according to N. I. Aronova et al, or the ALA hydrochloride according to DE-22 08 800-A2 and Izv. Akad. Nauk SSSR, Ser. Khim, 1973, pp 657/8. The same acid hydrolysis of keto esters prepared by the condensation of hippuric acid with an anhydride has been described by D. Evans et al in J. Chem. Soc., Chem. Comm., 1978, pp 753/4, but in which the reaction requires the formation of a dianion under anhydrous conditions. The hydrochloride of ALA is obtained in the same way by the acid hydrolysis of N-phthalimide derivatives of ALA, which are generally obtained by condensing a salt of phthalimide with a δ-bromine derivative (S. I. Zavyalov et al, Izv. Akad. Nauk SSSR, Ser. Khim., 1987, pp 1796–9; E. Benedikt et al, Z. Naturforsch, B: Anorg. Chem., Org. Chem., 1986, 41B, pp 1593/4; Z. Rykowski et al., Pol., 1979, PL 104118 and Rocz. Chem., 1977, 51, pp 1675–8).

The reduction of nitrosyl derivatives according to Z. Chabudzinski et al in Chem. Stosow., 1977, 21 pp 251–255 or acyl cyanides according to A. Pfaltz et al in Tetrahedron Lett., 1984, 25, pp 1977–2980 also leads to the ALA hydrochloride.

Biosynthetic processes for the preparation of ALA under different culture conditions are described by S. Nagai et al in JP 02261389-A2, Koesnandar in Biotechnol. Lett., 1989, 11, pp 567–572 and T. Sasaki et al in JP0292293-A2. However, these methods require highly dilute solutions and only give low ALA concentrations.

The problem of the present invention is to provide a simple process for the preparation of ALA and derivatives thereof with good yield and purity, the starting product being obtained from inexpensively available sugars.

According to the invention this problem is solved by a process for the preparation of N-acyl derivatives of ALA of general formula I:

R—CO—NH—CH₂—CO—CH₂=CH₂—COOH    (I), in which R stands for a lower alkyl group with 1 to 10 C-atoms, particularly a methyl, ethyl, propyl, isopropyl or butyl group or a phenyl, benzyl, furyl or furfuryl group, as described in the characterizing part of the main claim, or the hydrochloride of the free acid by acid hydrolysis according to subclaim 2, preferred process measures being described in the further subclaims.

The process is performed in three stages and is based on 5-hydroxymethyl furfural (HMF) obtained by the acid degradation of sugars.

In the first stage the HMF of formula II

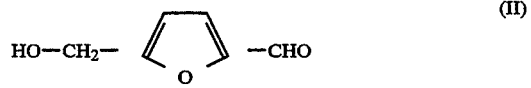

by condensing with a nitrile of formula III

R—C≡N    (III), in which the R radical has the above meaning, is transformed into the corresponding N-acyl-5-aminomethyl furfural of formula IV:

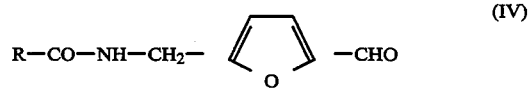

The acid-catalyzed condensation preferably takes place at a temperature of 0° to 50° C.. The acid used is a strong acid, preferably a mineral acid such as sulphuric or phosphoric acid, a sulphonic acid such as trifluoromethane sulphonic acid and in particular a mixture of trifluoromethane sulphonic acid/phosphoric acid anhydride. The molar ratio of HMF to the acid is preferably between 1:0.5 and 1:2. The molar ratio of HMF to the nitrile is preferably in the range 1:100 to 1:300.

In the second stage the N-acyl furan compound (IV) is oxidized to the corresponding furanone compound, namely to the N-acyl-5-aminomethyl-5-hydroxydihydro-2,5-furan-2-one of general formula V:

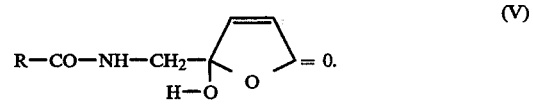

The oxidation of the corresponding N-acyl furan derivative (IV) is carried out by photooxidation by means of oxygen in the presence of a photosensitizer, particularly with rose Bengal deposited on a resin. A Sephadex QAE 25 resin (L. Cottier et al., Bull. Soc. Chim. Fr. 1986, pp 848–851) is particularly suitable, the rose Bengal concentration being approximately 10%. This oxidation is carried out at a temperature between 0° and 50° C. in a polar solvent such as methanol, ethanol, acetone, dichloromethane or tetrahydrofuran.

In the third stage the thus oxidized furanone of general formula V is reduced to the corresponding N-acyl derivative of ALA according to general formula I.

This reduction of the raw furanone preferably takes place with zinc in acetic acid at a temperature between 0° and 60° C., the heterogeneous mixture undergoing an ultrasonic treatment.

The process according to the invention makes it possible to prepare the N-acyl derivatives of ALA in three stages with a HMF-related total yield between 20 and 60%.

By acid hydrolysis of the N-acyl derivatives of general formula I the ALA hydrochloride is obtained with hydrochloric acid.

EXAMPLE 1

A. Preparation of the N-acyl Furan Compound (IV)

0.354 ml of an equimolar mixture of water (3.24 mmole) and trifluoromethane sulphonic acid (3.24 mmole) are added dropwise to a solution of 0.204 g of HMF (1.62 mmole) in 13 ml of acetonitrile kept at 25° C. The solution is diluted with 20 g of ice after 22 hours, neutralized with sodium hydrogen carbonate and extracted five times with in each case 20 ml of dichloromethane. The solvent is evaporated after drying over sodium sulphate. The raw product is chromatographically purified over silica gel and gives 120 mg (0.72 mmole) of N-acetyl-5-aminomethyl furfural (IV) corresponding to a yield of 47%, as well as 14 mg of unreacted HMF, so that the total conversion is 93%.

B. Preparation of the Furanone Compound (V)

A solution of 10 ml of ethanol and 405 mg (2.4 mmole) of the thus obtained N-acetyl derivative (IV) and 150 mg of rose Bengal on a Sephadex QAE 25 resin in 10% concentration is irradiated, under oxygen, with a 150 W tungsten halogen lamp. After absorbing the theoretical volume of 54 ml of oxygen, after approximately 4 hours the solution is allowed to stand for 12 hours and then filtered. Following evaporation the raw product contains 414 mg of N-acetyl-5-aminomethyl-5-hydroxydihydro-2,5-furan-2-one (IV) or 1-N-acetyl-aminomethyl-1-hydroxybutanenolide, which corresponds to a yield of 64%.

C. Preparation of the Acetyl Derivative of ALA

The thus obtained furanone raw product is added to 10 ml of acetic acid containing 966 mg of zinc powder. The mixture is exposed to ultrasonic treatment (160 W, 42 kHz) and after 2 hours is filtered and concentrated. The residue is chromatographically purified on silica gel and gives 243 mg (1.35 mmole) of N-acetyl-5-aminolevulinic acid, which corresponds to a 55% yield.

The total yield based on the reacted HMF corresponds to 24%.

EXAMPLE 2

Accompanied by stirring with hydrochloric acid, the thus obtained N-acetyl 5-aminolevulinic acid was refluxed for approximately six hours, cooled, filtered and concentrated in vacuo. The residue recrystallized from ethanol gave the 5-aminolevulinic hydrochloride in the form of a reddish, crystalline mass with a melting point of 146° to 147° C. and analytical values of C: 35.6; H: 6.02; N: 8.35 (theoretically for $C_5H_{10}NO_3Cl/C$: 35.83; H: 6.01; N:8.36).

We claim:

1. Process for the preparation of an N-acyl derivative of 5-aminolevulinic acid (ALA) of formula I $$R-CO-NH-CH_2-CO-CH_2-CH_2-COOH \quad (I)$$

in which R is methyl, ethyl, propyl, isopropyl, butyl, phenyl, benzyl, furyl or furfuryl, comprising reacting 5-hydroxymethyl furfural (HMF) of formula II

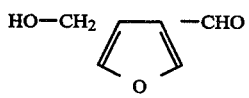

(II)

with a nitrile of formula III $$R-C≡N \quad (III)$$

in which R has the above meaning, in the presence of an acid catalyst to an N-acyl-5-amino-methyl furfural of formula IV

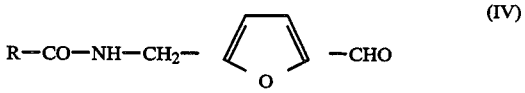

(IV)

in which R has the above meaning, and converting said N-acyl-5-aminomethyl-furfural by photooxidation into an N-acyl-5-aminomethyl-5-hydroxydihydro-2,5-furan-2-one of formula V

(V)

in which R has the above meaning, and reducing said furanone into the N-acyl levulinic acid of formula I.

2. A process according to claim 1 wherein in the condensation reaction of HMF with said nitrile a mineral acid, a sulphonic acid or a mixture of methane sulphonic acid and phosphoric anhydride is used as the acid catalyst.

3. Process according to claim 2, wherein the molar ratio of HMF to the acid catalyst is in the range of 1:0.5 to 1:2.

4. Process according to claim 2, wherein the molar ratio of HMF to nitrile is in the range of 1:100 to 1:300.

5. Process according to claim 2, wherein the condensation reaction is performed at a temperature between 0° and 50° C.

6. Process according to claim 1 wherein the photooxidation of the N-acyl-5-aminofurfural is performed by oxygen in the presence of a photosensitizer and at a temperature between 0° and 50° C.

7. Process according to claim 6, wherein the photooxidation is performed in a polar solvent.

8. Process according to claim 6, wherein during the photooxidation, rose Bengal in solution or deposited on a resinous carrier is used as the photosensitizer.

9. Process according to claim 1 wherein the reduction of N-acyl-5-aminomethyl-5-hydroxydihydro-2,5-furan-2-one is performed by zinc in acetic acid under ultrasonic treatment at a temperature between 0° and 60° C.

10. Process for preparing the hydrochloride of 5-aminolevulinic acid comprising reacting 5-hydroxymethyl furfural (HMF) of formula II

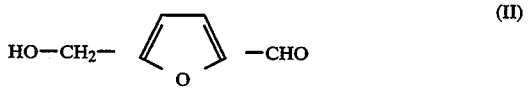

(II)

with a nitrile of formula III $$R-C≡N \quad (III)$$

where R is methyl, ethyl, propyl, isopropyl, butyl, phenyl, benzyl, furyl or furfuryl, in the presence of an acid catalyst to an N-acyl-5-amino-methyl furfural of formula IV

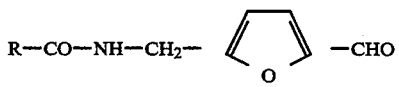 (IV)

in which R has the above meaning and converting said N-acyl-5-aminomethyl-furfural by photooxidation into an N-acyl-5-aminomethyl-5-hydroxydihydro-2,5-furan-2-one of formula V

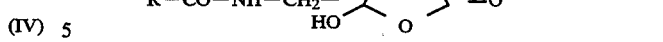 (V)

in which R has the above meaning, and reducing said furanone into an N-acyl derivative of 5-aminolevulinic acid (ALA) of formula I

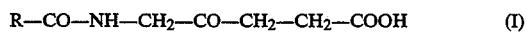 (I)

in which R has the above meaning, and acid hydrolyzing said acyl derivative of formula I with HCl.

11. Process according to claim 7, wherein said polar solvent is methanol, ethanol, acetone or dichloromethane.

* * * * *